United States Patent [19]

Wirth et al.

[11] 4,369,276
[45] Jan. 18, 1983

[54] PYRROLE STABILIZERS FOR CHLORINE-CONTAINING THERMOPLASTICS

[75] Inventors: Hermann O. Wirth; Jürgen Büssing, both of Bensheim; Hans-Helmut Friedrich, Lautertal, all of Fed. Rep. of Germany

[73] Assignee: Ciba-Geigy Corporation, Ardsley, N.Y.

[21] Appl. No.: 266,872

[22] Filed: May 26, 1981

Related U.S. Application Data

[63] Continuation-in-part of Ser. No. 164,194, Jun. 30, 1980, Pat. No. 4,290,940.

[30] Foreign Application Priority Data

Jun. 28, 1979 [CH] Switzerland ............... 6035/79

[51] Int. Cl.³ ............................................. C08K 5/34
[52] U.S. Cl. ...................................... 524/104; 524/94; 524/109; 524/114; 524/147; 524/178; 524/327; 524/394; 524/399
[58] Field of Search ............... 260/45.8 N; 524/104

[56] References Cited

U.S. PATENT DOCUMENTS 4,290,940 9/1981 Wirth et al. ................ 524/104

Primary Examiner—Lorenzo B. Hayes
Assistant Examiner—R. A. White
Attorney, Agent, or Firm—Harry Falber

[57] ABSTRACT

Chlorine-containing thermoplastics, containing a pyrrole of the formula I

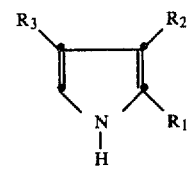

in which $R_1$ is hydrogen, alkyl, cycloalkyl, aryl, alkoxycarbonylmethyl, free or esterified α-hydroxyalkyl, free or esterified α-hydroxycycloalkylmethyl, free or esterified α-hydroxyaralkyl, alkoxymethyl, alkylthiomethyl, aryloxymethyl, arylthiomethyl, cycloalkoxymethyl, cycloalkylthiomethyl, aralkoxymethyl, aralkylthiomethyl, alkoxy, alkylthio, cycloalkoxy, cycloalkylthio, aralkoxy, arylalkylthio, aryloxy, arylthio, halogen, mercapto, mercaptomethyl or hydroxyl, $R_2$ is hydrogen, alkyl, cycloalkyl, aryl, free or esterified α-hydroxyalkyl, in which the alkyl moiety together with $R_1$ can be alkylene, or free or esterified α-hydroxycycloalkylmethyl, free or esterified α-hydroxyaralkyl, alkoxy, cycloalkoxy, aralkoxy, aryloxy, alkylthio, cycloalkylthio, aralkylthio, arylthio, alkoxymethyl, alkylthiomethyl, aryloxymethyl, arylthiomethyl, cycloalkoxymethyl, cycloalkylthiomethyl, aralkoxymethyl, aralkylthiomethyl, hydroxyl, cyano, free carboxyl or carboxyl in the form of a salt or an ester, or acyl, it being possible for acyl together with $R_1$ to be —CO-alkylene, in which —CO— is bonded in the 3-position, or $R_2$ is halogen, mercapto or mercaptomethyl, and $R_3$ is alkyl, cycloalkyl, aralkyl, aryl, free or esterified hydroxymethyl, alkoxymethyl, alkylthiomethyl, cycloalkoxymethyl, cycloalkylthiomethyl, aralkoxymethyl, aralkylthiomethyl, aryloxymethyl or arylthiomethyl, alkoxy, alkylthio, cycloalkoxy, cycloalkylthio, aralkoxy, aralkylthio, aryloxy, arylthio, halogen, mercapto or mercaptomethyl, or if $R_2$ is carboxyl in the form of a salt, $R_3$ is hydrogen and $R_1$ is as defined, or in which $R_3$ is hydroxyl and $R_1$ is hydrogen, alkyl or aryl and $R_2$ is hydrogen, alkyl, aryl or acyl, or a salt thereof.

6 Claims, No Drawings

PYRROLE STABILIZERS FOR CHLORINE-CONTAINING THERMOPLASTICS

This is a Continuation-in-part application of application Ser. No. 164,194 filed June 30, 1980 now U.S. Pat. No. 4,290,940.

The present invention relates to the stabilisation of chlorine-containing thermoplastics by the addition of pyrroles, and also to novel pyrroles.

It is known that chlorine-containing polymers must be protected against the harmful influence of light and heat, for example when processing to mouldings. Hitherto, in particular organo-tin compounds, metal carboxylates or aminocrotonates have been used for this purpose. However, the stabilities achieved with these active compounds are not always adequate for practical purposes and there is a need to find improvements here and in particular to provide better metal-free heat stabilisers for PVC. One stabiliser for PVC which has been known for a long time is 2-phenylindole, cf. Voigt "Stabilisierung der Kunststoffe" ("Stabilisation of Plastics"), Springer-Verlag, 1966, page 306, but this gives satisfactory results only in combination with metal carboxylates.

U.S. Pat. Nos. 3,404,159, 3,573,216 and 3,404,161 disclose pyrrole-malonitriles which are suitable as UV absorbers and light stabilisers, inter alia also for PVC, because of their specific absorption between 250 and 400 mμ. U.S. Pat. No. 3,478,053 discloses 2,3-diarylpyrroles for the same purpose. These patent specifications were not able to contribute to the development of improved heat stabilisers, which was the object of the present invention.

The invention relates to chlorine-containing thermoplastics, containing a pyrrole of the formula I

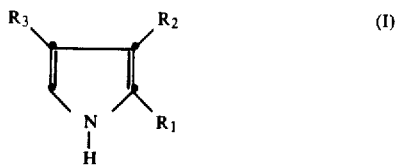

in which $R_1$ is hydrogen, alkyl, cycloalkyl, aryl, alkoxycarbonylmethyl, free or esterified α-hydroxyalkyl, free or esterified α-hydroxycycloalkylmethyl, free or esterified α-hydroxyaralkyl, alkoxymethyl, alkylthiomethyl, aryloxymethyl, arylthiomethyl, cycloalkoxymethyl, cycloalkylthiomethyl, aralkoxymethyl, aralkylthiomethyl, alkoxy, alkylthio, cycloalkoxy, cycloalkylthio, aralkoxy, arylalkylthio, aryloxy, arylthio, halogen, mercapto, mercaptomethyl or hydroxyl, $R_2$ is hydrogen, alkyl, cycloalkyl, aryl, free or esterified α-hydroxyalkyl, in which the alkyl moiety together with $R_1$ can be alkylene, or free or esterified α-hydroxycycloalkylmethyl, free or esterified α-hydroxyaralkyl, alkoxy, cycloalkoxy, aralkoxy, aryloxy, alkylthio, cycloalkylthio, aralkylthio, arylthio, alkoxymethyl, alkylthiomethyl, aryloxymethyl, arylthiomethyl, cycloalkoxymethyl, cycloalkylmethyl, aralkoxymethyl, aralkylthiomethyl, hydroxyl, cyano, free carboxyl or carboxyl in the form of a salt or an ester, or acyl, it being possible for acyl together with $R_1$ to be —CO-alkylene, in which —CO— is bonded in the 3-position, or $R_2$ is halogen, mercapto or mercaptomethyl, and $R_3$ is alkyl, cycloalkyl, aralkyl, aryl, free or esterified hydroxymethyl, alkoxymethyl, alkylthiomethyl, cycloalkoxymethyl, cycloalkylthiomethyl, aralkoxymethyl, arylalkylthiomethyl, aryloxymethyl or arylthiomethyl, alkoxy, alkylthio, cycloalkoxy, cycloalkylthio, aralkoxy, aralkylthio, aryloxy, arylthio, halogen, mercapto or mercaptomethyl, or if $R_2$ is carboxyl in the form of a salt, $R_3$ is hydrogen, and $R_1$ is as defined, or in which $R_3$ is hydroxyl and $R_1$ is hydrogen, alkyl or aryl and $R_2$ is hydrogen, alkyl, aryl or acyl, or a salt thereof.

It has been found, surprisingly, that the pyrroles used according to the invention are outstandingly effective stabilisers, in particular for PVC, which do not have the disadvantages of the prior art or do not have the disadvantages to the same degree, and in particular do not necessarily have to be combined with metal compounds.

Alkyl $R_1$ has, in particular, 1-6 C atoms, such as ethyl, n-propyl or in particular methyl. Cycloalkyl $R_1$ has, in particular 5-8 C atoms and is, in particular, cyclohexyl or cyclopentyl. Aryl $R_1$ is phenyl, which can be substituted, for example by $C_{1-6}$ alkyl, such as methyl, $C_{1-6}$alkoxy, such as methoxy, and/or hydroxyl, and is, for example, m-hydroxyphenyl and in particular phenyl itself. Alkoxycarbonylmethyl $R_1$ has, in particular, 1-18 C atoms in the alkoxy moiety, such as methoxycarbonylmethyl or ethoxycarbonylmethyl. α-Hydroxyalkyl $R_1$ has, in particular, 1-6 C atoms, such as hydroxymethyl or α-hydroxyethyl, and is in particular esterified with alkylcarbonyl or arylcarbonyl, as indicated for $R_2$. α-Hydroxycycloalkylmethyl $R_1$ has, in particular, 6-12 C atoms, such as hydroxy-(cyclohexyl)-methyl, and can be esterified as indicated above. α-Hydroxyaralkyl $R_1$ has, in particular, 7-12 C atoms, such as α-hydroxybenzyl, and can be esterified as indicated above. Cycloalkoxymethyl $R_1$ has, in particular, 6-12 C atoms, such as cyclohexyloxymethyl, and the same applies in the case of cycloalkylthiomethyl. Aralkoxymethyl or aralkylthiomethyl $R_1$ has, in particular, 8-13 C atoms, such as benzyloxymethyl. Alkoxy $R_1$ has, in particular, 1-6 C atoms, such methoxy. Alkylthio $R_1$ has, in particular, 1-6 C atoms, such as methylthio. Alkoxymethyl and alkylthiomethyl $R_1$ have, in particular 1-18 C atoms in the alkyl moiety, such as methoxymethyl, ethoxymethyl, methylthiomethyl or ethylthiomethyl. Aryloxymethyl and arylthiomethyl $R_1$ are, in particular, those radicals in which aryl is substituted or unsubstituted phenyl, such as phenoxymethyl or phenylthiomethyl. What has been stated with regard to $R_1$ applies equally in the case of $R_2$ and $R_3$ when these are the radicals defined for $R_1$. Halogen $R_1$, $R_2$ and $R_3$ are, for example, bromine, fluorine and in particular chlorine.

As carboxyl in the form of a salt, $R_2$ is, in particular, carboxyl which has been converted to a salt with one equivalent of calcium, barium, zinc, cadmium, antimony, diorgano-tin, such as dialkyl-tin, or in particular magnesium.

Acyl $R_2$ is in particular formyl, alkoxycarbonyl, arylcarbonyl or free, esterified or amidated carboxyl.

Alkylcarbonyl $R_2$ is, in particular, alkylcarbonyl having 2-19 C atoms, such propionyl, butyryl, lauroyl or in particular acetyl. Arylcarbonyl $R_2$ is in particular arylcarbonyl having 7-19 C atoms, such as substituted or unsubstituted benzoyl and in particular benzoyl itself. Esterified carboxyl $R_2$ is in particular carboxyl esterified with a monohydric to tetrahydric aliphatic, cycloaliphatic or araliphatic alcohol having 1-20 C atoms, and preferably a dihydric alcohol is esterified with two pyrrolecarboxylic acid molecules, a trihydric alcohol is esterified with three pyrrolecarboxylic acid molecules and a tetrahydric alcohol is esterified with four pyrrolecarboxylic acid molecules. Suitable monohydric alcohols are, for example, $C_1$–$C_{18}$-alkanols, such as methanol, ethanol, n-octanol or lauryl alcohol, $C_5$–$C_{19}$-aralkanols, such as benzyl alcohol or furfuryl aclohol, or $C_5$–$C_8$-cycloalkanols, such as cyclohexanol. Suitable dihydric alcohols are, for example, $C_2$–$C_{20}$-alkanediols, such as ethylene glycol or 1,2-butylene glycol, $C_{4-20}$-oxaalkanediols, such as 3-oxa-1,5-dihydroxypentane, or $C_{4-20}$-thiaalkanediols, such as 3-thia-1,5-dihydroxy-pentane. Suitable trihydric alcohols are, for example, $C_{3-20}$-alkanetriols, such as glycerol, or tris$\beta$-hydroxyethyl isocyanurate, and suitable tetrahydric alcohols are, for example, $C_{4-20}$-alkanetetrols, such as pentaerythritol. ($C_{1-18}$-Alkoxy)-carbonyl $R_2$ is particularly preferred. Amidated carboxyl $R_2$ is, in particular, arylaminocarbonyl, in which aryl has in particular 6–18 C atoms, such as phenylaminocarbonyl, which can be substituted, for example by $C_{1-6}$ alkyl, $C_{1-6}$ alkoxy and/or hydroxyl, and in particular phenylaminocarbonyl itself or m-hydroxyphenylaminocarbonyl, or ($C_{1-18}$-alkyl)-aminocarbonyl, such as methylaminocarbonyl or ethylaminocarbonyl. Suitable alcohols in esterified carboxyl are, in particular, also those containing epoxy groups, such as monohydric alcohols of this type, for example a glycidyl ester or an epoxidised oleyl ester.

If $R_2$ together with $R_1$ is —CO-alkylene, alkylene has, in particular, 2–10 C atoms and 2 or 3 chain C atoms, such as ethylene, 1,3-propylene or 2,2-dimethyl-1,3-propylene.

As alkyl, aryl, alkoxymethyl, alkylthiomethyl, aryloxymethyl and arylthiomethyl, $R_3$ is, in particular, the radicals defined under $R_1$, $R_3$ and $R_1$ being independent of one another, and is in particular methyl or alkoxymethyl and especially phenyl.

Salts of pyrroles of the formula I are, in particular, N-metal salts, such as have been mentioned for carboxyl $R_2$ in the form of a salt, such pyrroles which have been converted to a salt with one equivalent of calcium, barium, zinc, cadmium, antimony, diorgano-tin, such as dialkyl-tin, for example di-n-butyl-tin, or in particular magnesium.

Preferably, the chlorine-containing thermoplastics according to the invention contain those pyrroles of the formula I in which $R_1$ is phenyl, $R_2$ is hydrogen or methyl and $R_3$ is phenyl, and especially also those in which $R_1$ is methyl, $R_2$ is a carboxyl mono-esterified to tetra-esterified with a monohydric to tetrahydric $C_{1-20}$ alcohol, or aminocarbonyl or arylaminocarbonyl and $R_3$ is aryl, and in particular those in which $R_1$ is methyl, $R_2$ is as defined above and $R_3$ is phenyl.

The pyrroles of the formula I which are used are in particular those in which $R_1$ is hydrogen, alkyl, cycloalkyl, aryl, alkoxycarbonylmethyl, hydroxymethyl, alkoxymethyl, alkylthiomethyl, aryloxymethyl or arylthiomethyl, $R_2$ is cyano, free carboxyl or carboxyl in the form of a salt, or acyl, it being possible for acyl together with $R_1$ to be —CO—alkylene, in which —CO— is bonded in the 3-position, and $R_3$ is alkyl, aryl, hydroxymethyl, alkoxymethyl, alkylthiomethyl, aryloxymethyl or arylthiomethyl.

Pyrroles of the formula I which are particularly preferentially used are those in which $R_1$ is methyl or phenyl, $R_2$ is cyano, $C_{2-19}$-alkylcarbonyl, $C_{7-19}$-arylcarbonylor carboxyl which is esterified with a $C_{1-18}$-alkanol, $C_{5-8}$-cycloalkanol, $C_{5-19}$-aralkanol, $C_{2-20}$-alkanediol or $C_{4-20}$-thiaalkanediol or with pentaerythritol, and $R_3$ is methyl, phenyl or ($C_{1-18}$-alkoxy)-methyl.

Preferably, the pyrroles of the formula I which are used are those in which $R_1$ is methyl, $R_2$ is $C_{2-19}$-alkylcarbonyl or in particular carboxyl which is esterified with a $C_{1-18}$-alkanol, $C_{2-20}$-alkanediol or $C_{4-20}$-thiaalkanediol or with pentaerythritol, and $R_3$ is phenyl, and in particular the pyrroles mentioned in the examples, and amongst the latter especially:

(a) 2-methyl-3-cyclohexyloxycarbonyl-4-phenyl-pyrrole,
(b) 2-methyl-3-benzyloxycarbonyl-4-phenyl-pyrrole,
(c) 2-phenyl-3-ethoxycarbonyl-4-methyl-pyrrole,
(d) 2-methyl-3-benzoyl-4-phenyl-pyrrole,
(e) 2-methyl-3-ethoxycarbonyl-4-phenyl-pyrrole,
(f) 2,4-diphenyl-pyrrole,
(g) 2-methyl-3-phenylaminocarbonyl-4-phenyl-pyrrole,
(h) 2-methyl-3-meta-hydroxyphenylaminocarbonyl-4-phenyl-pyrrole and,
(i) 2,4-diphenyl-3-($\alpha$-hydroxy-ethyl)-pyrrole.

Pyrroles are compounds which have been known for a long time. Thus, in Ber. 35, 3,004 (1902) Knorr and Lange describe the preparation of pyrroles by reaction of aminoketones, such as aminoacetophenone or aminoacetone, with an acylacetone, such as ethyl acetoacetate or acetylacetone. Thus, 2,4-dimethyl-3-ethoxycarbonyl-pyrrole is obtained from aminoacetone and ethyl acetoacetate, and 2,4-dimethyl-3-acetyl-pyrrole is obtained from aminoacetone and acetylacetone. The reaction is advantageously carried out in the presence of a buffer, such as sodium acetate/acetic acid. According to Benary, Ber. 44, 405 (1911) it is also possible in the above reaction to replace the aminoketone by a chloroaldehyde and ammonia, such as by chloroacetaldehyde and ammonia, for example in the form of a 10% ammonia solution. In the case of chloroacetaldehyde, 2,3-substituted pyrroles are obtained, for example 2-methyl-3-ethoxycarbonylpyrrole is obtained from chloroacetaldehyde, ammonia and ethyl acetoacetate. A summary of pyrrole chemistry is published in the monograph by R. A. Jones, "The Chemistry of Pyrroles", Academic Press 1977.

The pyrroles are incorporated in the chlorine-containing thermoplastics to be stabilised before the latter are processed in conventional devices and in general are incorporated in amounts of 0.05 to 5 and preferably of 0.1 to 3% by weight, based on the chlorine-containing thermoplastics.

A better stabilizing effect can be obtained by the further addition of at least one of the conventional PVC stabilizers in the customary amounts, such as epoxy compounds, preferably epoxydised fatty acid esters, such as epoxydised soya bean oil, phosphites, metal carboxylate or phenolate stabilizers, such as calcium or barium carboxylates, especially calcium stearate, and also carboxylates of zinc or cadmium, or organo-tin compounds. Suitable metal carboxylates or phenolates are those of carboxylic acids having 8 to 20 C atoms or phenols having 6 to 20 C atoms.

Particularly suitable conventional phosphites are those of the general formula II, III or IV

-continued

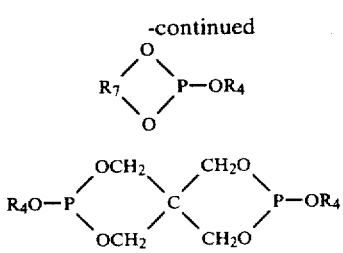

wherein each of $R_4$, $R_5$ and $R_6$ independently is $C_1-C_{18}$ alkyl, $C_1-C_{20}$ alkenyl, $C_5-C_7$ cycloalkyl, $C_6-C_{12}$ aryl, $C_7-C_{19}$ alkaryl which is unsubstituted or substituted by hydroxy or by $C_1-C_4$ alkoxy and $R_7$ is $C_2-C_6$ alkylene, which is unsubstituted or substituted by $C_1-C_{18}$ alkyl, $C_2-C_{13}$ alkoxymethyl or alkylthiomethyl or by phenyl or is $C_6-C_{10}$ arylene which is unsubstituted or substituted by $C_1-C_4$ alkyl or is $C_5-C_7$ cycloalkylene.

$R_4$, $R_5$ and $R_6$ as $C_1-C_{18}$ alkyl are e.g. methyl, ethyl, n-propyl, isopropyl, n-butyl, sec.-butyl, tert.-butyl, n-pentyl, n-hexyl, n-octyl, n-nonyl, decyl, dodecyl, tetradecyl, hexadecyl or octadecyl. Preferred alkyl groups contain 8–18 carbon atoms.

$R_4$, $R_5$ and $R_6$ as $C_1-C_{20}$ alkenyl are e.g. allyl, 2-butenyl, pentenyl, hexenyl, heptenyl or oleyl.

$R_4$, $R_5$ and $R_6$ as aryl can be naphthyl, biphenyl or preferably phenyl.

$R_4$, $R_5$ and $R_6$ as $C_7-C_{19}$ alkaryl which is unsubstituted or substituted by hydroxy or $C_1-C_4$ alkoxy are e.g. tolyl, ethylphenyl, xylyl, cumyl, cymyl, cresyl, 4-methoxyphenyl, 2,4-dimethoxyphenyl, alkoxyphenyl or butoxyphenyl.

$R_4$, $R_5$ and $R_6$ as $C_5-C_7$ cycloalkyl are e.g. cyclopentyl, cycloheptyl and preferably cyclohexyl.

$R_7$ as $C_2-C_6$ alkylene which is unsubstituted or substituted by $C_1-C_{18}$ alkyl or phenyl is e.g. ethylene, propylene or hexamethylene which can be unsubstituted or substituted by methyl, ethyl, propyl, isopropyl, butyl, hexyl, decyl, dodecyl, tetradecyl, octadecyl or phenyl and is preferably 2-propyl-2-methyl-propylene, 1-propyl-2-ethyl-propylene or phenylethylene.

$R_7$ as $C_2-C_6$ alkylene which is substituted by $C_2-C_{13}$ alkoxymethyl or alkylthiomethyl is e.g. ethoxymethylethylene, butoxymethylethylene, octyloxymethylethylene or dodecylthiomethylethylene.

$R_7$ as $C_6-C_{10}$ arylene which is unsubstituted or substituted by $C_1-C_4$ alkyl is preferably tert.-butylphenylene or unsubstituted phenylene.

$R_7$ as $C_5-C_7$ cycloalkylene is preferably cycloalkylene.

Preferred phosphites of the formula IV are those wherein $R_4$ is $C_1-C_{18}$ alkyl, perferably $C_8-C_{18}$ alkyl and most perferably octyl or decyl.

Particularly suitable phosphites are trioctylphosphite, tridecylphosphite, tridodecylphosphite, tritetradecylphosphite, tristearykphosphite, trioleylphosphite, triphenylphosphite, tricresylphosphite, tris-p-nonylphenylphosphite, or tricyclohexylphosphte. The most preferred phosphites are aryldialkylphosphites and alkyldiarylphosphites as e.g. phenyldidecylphosphite, nonylphenyldidecylphosphite, (2,4di-tert.-butylphenyl)-di-dodecylphosphite or (2,6-di-tert.-butylphenyl)-di-dodecylphosphite.

A good stabilising effect is obtained by using, in addition to the pyrroles of the formula I, at least one epoxy compound, and/or a metal carboxylate or phenolate of a metal of the second main group of the Periodic Table, preferably a calcium carboxylate such as calcium stearate. An even better stabilising effect is obtained by additionally using at least one of the phosphites defined above, or at least one zinc or cadmium carboxylate or an organotin compound. Preferred organotin compounds are mono-organotin compounds.

It is possible, however, to obtain a particularly good stabilising effect by stabilising the chlorinated thermoplastics with a mixture of at least one pyrrole of the formula I, at least one epoxy compound, and/or a metal carboxylate or phenolate of a metal of the second main group of the Periodic Table, at least one zinc or cadmium carboxylate or an organotin compound, and at least one of the phosphites defined above.

Surprisingly, even a relatively small concentration of pyrrole of the formula I ensures an excellent stabilisation under these conditions.

Costabilizers are preferably incorporated in amounts of 0.05 to 5 and especially 0.1 to 3% by weight, based on the chlorine-containing thermoplastics.

The ratio of pyrrole to costabilizers can be about 2:1 to 1:8.

Vinyl chloride polymers or copolymers are preferably used for the moulding compositions according to the invention. Preferred polymers are suspension polymers and mass polymers and washed emulsion polymers, i.e. emulsion polymers with a low emulsifier content. Suitable comonomers for the copolymers are, for example: vinyl acetate, vinylidene chloride, trans-dichloroethylene, ethylene, propylene, butylene, maleic acid, acrylic acid, fumaric acid and itaconic acid. Further suitable chlorine-containing polymers are post-chlorinated PVC and chlorinated polyolefins, and also graft polymers of PVC with EVA and MBS.

The stabilised thermoplastics according to the invention are prepared by known processes, by incorporating the stabilisers and, if desired, further stabilisers into the polymer. A homogeneous mixture of stabiliser and PVC can be obtained, for example, with the aid of a two-roll mixer at 150°–210° C.

Depending on the intended use of the moulded composition, it is also possible to incorporate further additives before or at the same time as incorporating the stabiliser; such additives are, for example, lubricants (preferably montan waxes or glycerol esters), fatty acid esters, paraffins, plasticisers, fillers, modifiers (such as additives which impart high impact strength), pigments, light stabilisers, UV absorbers, antioxidants or further costabilisers, for example phosphites. The thermoplastics according to the invention can be processed to mouldings by the shaping process customary for this purpose, for example by extrusion, injection moulding or calendering. Use as plastisols is also possible.

The heat stabilisation with the stabilisers used according to the invention is outstanding in the thermoplastics according to the invention. The stability to light is also good.

The examples which follow serve to illustrate the invention in more detail. Parts and percentages are by weight.

EXAMPLES 1–7

General synthesis example

A mixture of 0.1 mol of α-aminoketone hydrochloride *), 0.12 mol of sodium acetate and 0.1 mol of ethyl acetoacetate or 1,3-diketone in 100 g of 75% acetic acid is heated on a waterbath for 1 hour, with stirring. After cooling, the reaction mixture is stirred into cold water and the reaction product which has precipitated is filtered off with suction and recrystallised.

*) in place of the aminoketone hydrochloride it is also possible to use an α-nitrosoketone, which under the reaction conditions—if a suitable reducing agent is used—is reduced to the α-aminoketone and simultaneously reacted.

In the case of reaction products which are obtained as oily or liquid products, the aqueous solution is extracted with toluene or chloroform, the toluene solution is dried over sodium sulfate and filtered, the filtrate is concentrated by means of a rotary evaporator and the residue is distilled (high vacuum) or recrystallised.

In addition to known pyrrole derivatives, the following pyrrole derivatives which have not previously been described have also been synthesised by this process.

2-Methyl-3-carboxymethyl-4-phenylpyrrole (Example 1, stabiliser No. 10), melting point 132°–133° C.; structure established by $^{13}$C-NMR spectroscopy.

2-Methyl-3-carboxylauryl-4-phenylpyrrole (Example 2, stabiliser No. 5), melting point 51°–52° C.; structure established by $^{13}$C-NMR spectroscopy.

Thiodiethylene glycol bis-(2-methyl-4-phenylpyrrole-3-carboxylate) (Example 3, stabiliser No. 9), melting point 161°–163° C.; structure established by $^{13}$C-NMR spectroscopy. 2,4-Diphenyl-3-(α-hydroxyethyl)-pyrrole, melting point 128° C. (Example 4, stabiliser No. 15).

2-Methyl-3-phenylaminocarbonyl-4-phenyl-pyrrole (Example 5, stabiliser No. 14).

2-Methyl-3-meta-hydroxyphenylaminocarbonyl-4-phenyl-pyrrole (Example 6).

2-Methyl-3-cyclohexyl-oxycarbonyl-4-phenyl-pyrrole (Example 7, stabiliser No. 12).

EXAMPLE 8

Test data based on DIN 53,381, sheet 3 (dehydrochlorination test) for stabilisers according to the invention Concentration: concentration based on PVC (S-PVC, K value 64)

Induction time: time which elapses before the dehydrochlorination curve starts to rise Elimination time: time which elapses before 0.5% of the available chlorine has been eliminated Tangent: gradient of the curve at "elimination time 0.5%".

| Stabiliser No. | Stabiliser(s) | Concentration [%] | Induction time [min.] | Elimination time [min.] | Tangent |
|---|---|---|---|---|---|
| Comparison | None | — | 12 | 40 | 0.93 |
| 1 | H₃C, CO—CH₃, CH₃ pyrrole (N-H) | 0.34* | 23 | 68 | 0.55 |
| 2 | H₃C, CO—O—Et, CH₃ pyrrole (N-H) | 0.42* | 16 | 50 | 0.74 |
| 3 | Ph, CO—CH₃, CH₃ pyrrole (N-H) | 0.50* | 20 | 83 | 0.41 |
| 4 | Ph, CO—O—Et, CH₃ pyrrole (N-H) | 0.57* | 20 | 100 | 0.33 |
| Comparison | Epoxidised soya bean oil = ESO | 1.0 | 19 | 52 | 0.76 |
| 4 | Ph, CO—O—Et, CH₃ pyrrole (N-H) + ESO | 1.0 / 0.58 | 35 | 119 | 0.31 |
| 5 | Ph, CO—O—Lau, CH₃ pyrrole (N-H) + ESO | 1.0 / 0.94 | 32 | 115 | 0.31 |

-continued

| Stabiliser No. | Stabiliser(s) | Concentration [%] | Induction time [min.] | Elimination time [min.] | Tangent |
|---|---|---|---|---|---|
| 6 | ![pyrrole with H3C, CO-O-Et, Ph substituents] ESO + | 1.0 0.58 | 32 | 91 | 0.38 |
| 7 | ![pyrrole with Ph, CO-CH3, CH2-CO-O-CH3 substituents] ESO + | 1.0 0.68 | 23 | 88 | 0.40 |
| 8 | ![pyrrole with Ph, CO-Ph, CH3 substituents] ESO + | 1.0 0.65 | 30 | 98 | 0.38 |
| 9 | ![pyrrole with Ph, (CO-O-CH2-CH2-)2S, CH3 substituents] ESO + | 1.0 0.61 | 32 | 110 | 0.28 |
| 10 | ![pyrrole with Ph, CO-O-CH3, CH3 substituents] ESO + | 1.0 0.54 | 35 | 125 | 0.30 |
| 11 | ![pyrrole with Ph, CO-O-Et, Ph substituents] ESO + | 1.0 0.73 | 42 | 130 | 0.25 |
| Comparison | Epoxidised soya bean oil = ESO | 2.0 | 26 | 64 | 0.67 |
| 4 | ![pyrrole with Ph, CO-O-Et, CH3 substituents] ESO + | 2.0 1.0 | 40 | 152 | 0.23 |
| 4 | ![pyrrole with Ph, CO-O-Et, CH3 substituents] ESO + Ph—O—P(—O—C10H21)2 | 2.0 0.75 0.75 | 55 | 142 | 0.30 |
| Comparison | Epoxidised soya bean oil Ca stearate Zn stearate | 3.0 0.2 0.2 | 29 | 45 | 1.63 |
| 1 | Epoxidised soya bean oil Ca stearate Zn stearate ![pyrrole with Ph, CO-CH3, CH3 substituents] + | 3.0 0.2 0.2 0.4 | 47 | 65 | 1.44 |
| 4 | Epoxidized soya bean oil Ca Stearate | 3.0 0.2 | 49 | 75 | 1.0 |

| Stabiliser No. | Stabiliser(s) | | Concentration [%] | Induction time [min.] | Elimination time [min.] | Tangent |
|---|---|---|---|---|---|---|
| | Zn stearate | | 0.2 | | | |
| | 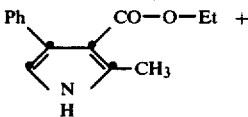 | + | | | | |
| 4 | 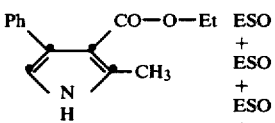 | ESO + ESO + ESO + | 0.5 0.5 1.0 1.0 1.5 1.5 | 29 35 40 | 107 125 140 | 0.33 0.29 0.26 |

*corresponding to 2.5 mmols per 100 g of PVC

EXAMPLE 9

Test results for compounds according to the invention in the static heating test at 180° C. S-PVC+2% of expoxidised soy bean oil+2.5 mmol% of stabiliser.

| Stabiliser No. | Stabilisers | Yellowness indices | | |
|---|---|---|---|---|
| | | Mill hide | 10 mins. | 20 mins |
| 12 | 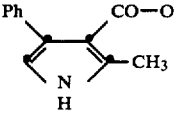 | 5.4 | 16.7 | 28.7 |
| 13 | 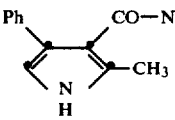 | 8.1 | 21.5 | 38 |
| 14 | 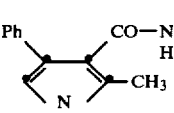 | 5.4 | 18.2 | 34 |
| 15 | 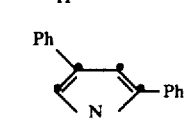 | 4.4 | 12.0 | 21.3 |

EXAMPLES 10-23

A dry blend consisting of 100 part of S-PVC (K-value 64) and stabilizers as indicated in the following examples 10-23 is rolled on a mixer roll for 5 minutes at 180° C. Samples having a thickness of 0.3 mm are taken from the rolled sheet obtained. The samples are subjected to heat in an oven at 180° C. and every 10 minutes the thermal ageing of a sample is determined according to the Yellowness Index (YI) of ASTM D 1925-70. The results are reported in the correspondent tables.

EXAMPLE 10

Stabilizer: 0,55 parts 2,4-diphenylpyrrole

| Yellowness Index after | | | |
|---|---|---|---|
| 0 min. | 10 min. | 20 min. | 30 min. |
| 3,3 | 14 | >100 | |

EXAMPLE 11

Stabilizers: 0,55 parts 2,4-diphenylpyrrole
2 parts epoxidised soya bean oil.

| Yellowness Index after | | | | | | | |
|---|---|---|---|---|---|---|---|
| 0 min. | 10 min. | 20 min. | 30 min. | 40 min. | 50 min. | 60 min. | 70 min. |
| 3,9 | 7,6 | 16,4 | 21 | 38 | 51 | 77 | >100 |

EXAMPLE 12

Stabilizers: 0,55 parts 2,4-diphenylpyrrole
2 parts epoxidised soya bean oil
0,55 parts phenyl-didecylphosphite

| Yellowness Index after | | | | | | | | |
|---|---|---|---|---|---|---|---|---|
| 0 min. | 10 min. | 20 min. | 30 min. | 40 min. | 50 min. | 60 min. | 70 min. | 80 min. |
| 2,2 | 3,8 | 9,2 | 15 | 25 | 30 | 56 | 79 | >100 |

EXAMPLE 13

Stabilizers: 0,55 parts 2,4-diphenylpyrrole
2 parts epoxidised soya bean oil
0,35 parts calcium stearate
0,15 parts zinc stearate

| Yellowness Index after | | | | | | | | |
|---|---|---|---|---|---|---|---|---|
| 0 min. | 10 min. | 20 min. | 30 min. | 40 min. | 50 min. | 60 min. | 70 min. | 80 min. |
| 3,8 | 7,1 | 11 | 13 | 21 | 23 | 44 | 64 | 83 |

EXAMPLE 14

Stabilizers 0,55 parts 2,4-diphenylpyrrole
2 parts epoxidised soya bean oil
0,35 parts calcium stearate
0,55 parts phenyl didecylphosphite
0,15 parts zinc stearate

| Yellowness Index after | | | | | | | | |
|---|---|---|---|---|---|---|---|---|
| 0 min. | 10 min. | 20 min. | 30 min. | 40 min. | 50 min. | 60 min. | 70 min. | 80 min. |
| 3,1 | 4,8 | 6,4 | 7,9 | 14 | 17 | 32 | 60 | 82 |

EXAMPLE 15

Stabilizers: 0,3 parts 2-methyl-3-aminocarbonyl-4-phenyl-
pyrrole
3 parts epoxidised soya bean oil
0,35 parts calcium stearate
0,15 parts zinc stearate
0,8 parts tridecylphosphite

| Yellowness Index after | | | | | |
|---|---|---|---|---|---|
| 0 min. | 10 min. | 20 min. | 30 min. | 40 min. | 50 min. |
| 6,1 | 8,6 | 16 | 26 | 65 | >100 |

EXAMPLE 16

Stabilizers: 0,3 parts 2-methyl-3-aminocarbonyl-4-phenyl-
pyrrole
3 parts epoxidised soya bean oil
0,35 parts calcium stearate
0,15 parts zinc stearate
0,8 parts phenyl didecylphosphite

| Yellowness Index after | | | | | |
|---|---|---|---|---|---|
| 0 min. | 10 min. | 20 min. | 30 min. | 40 min. | 50 min. |
| 6,4 | 11,5 | 21 | 31 | 53 | 84 |

EXAMPLE 17

Stabilizers: 0,3 parts 2-methyl-3-(3-hydroxyanilinocar-
bonyl)-4-phenylpyrrole
3 parts epoxidised soya bean oil
0,35 parts calcium stearate
0,15 parts zinc stearate
0,8 parts tridecylphosphite

| Yellowness Index after | | | | | | | | |
|---|---|---|---|---|---|---|---|---|
| 0 min. | 10 min. | 20 min. | 30 min. | 40 min. | 50 min. | 60 min. | 70 min. | 80 min. |
| 10 | 17 | 23 | 27 | 44 | 67 | 81 | | |

EXAMPLE 18

Stabilizers: 0,3 parts 2-methyl-3-(3-hydroxyanilino-car-
bonyl)-4-phenylpyrrole
3 parts epoxidised soya bean oil
0,35 parts calcium stearate
0,15 parts zinc stearate
0,8 parts phenyl didecylphosphite

| Yellowness Index after | | | | | | | |
|---|---|---|---|---|---|---|---|
| 0 min. | 10 min. | 20 min. | 30 min. | 40 min. | 50 min. | 60 min. | 70 min. |
| 11 | 17 | 20 | 23 | 29 | 38 | 58 | 77 |

EXAMPLE 19

Stabilizers: 0,57 parts 2-methyl-3-athyloxycarbonyl-4-phenyl-
pyrrol

| Yellowness Index after | | | | |
|---|---|---|---|---|
| 0 min. | 10 min. | 20 min. | 30 min. | 40 min. |
| 10 | 34 | 73 | 89 | >100 |

EXAMPLE 20

Stabilizers: 0,57 parts 2-methyl-3-athyloxycarbonyl-4-phen-
ylpyrrole
2 parts calcium stearate

| Yellowness Index after | | | | | | |
|---|---|---|---|---|---|---|
| 0 min. | 10 min. | 20 min. | 30 min. | 40 min. | 50 min. | 60 min. |
| 10,3 | 23 | 34 | 47 | 56 | 78 | >100 |

EXAMPLE 21

Stabilizer: 0,71 parts 2-methyl-3-cyclohexyloxy-carbonyl-
4-phenylpyrrole

| Yellowness Index after | | | | | |
|---|---|---|---|---|---|
| 0 min. | 10 min. | 20 min. | 30 min. | 40 min. | 50 min. |
| 9,3 | 29 | 51 | 72 | 89 | >100 |

EXAMPLE 22

Stabilizers: 0,71 parts 2-methyl-3-cyclohexyloxy-carbonyl-
4-phenylpyrrole
3 parts tridecylphosphite

| Yellowness Index after | | | | | | |
|---|---|---|---|---|---|---|
| 0 min. | 10 min. | 20 min. | 30 min. | 40 min. | 50 min. | 60 min. |
| 3,5 | 11 | 17 | 25 | 29 | 42 | >100 |

EXAMPLE 23

Stabilizers: 0,55 parts 3,4-diphenylpyrrole
2 parts epoxidised soya bean oil

| Yellowness Index after | | | | | |
|---|---|---|---|---|---|
| 0 min. | 10 min. | 20 min. | 30 min. | 40 min. | 50 min. |
| 37 | 51 | 69 | 85 | 94 | >100 |

EXAMPLE 24

A dry blend consisting of 100 parts of S-PVC (K-value 58), 4 parts of epoxidised soya bean oil, 0.35 parts of calcium stearate, 0.15 parts of zinc stearate, 0.3 parts of phenyl-didecylphosphite, 0.7 parts of a combined lubricant (low molecular polyethylene, stearyl alcohol and stearyl stearate), 0.5 parts of a flow auxiliary (copolymer of acrylate and methacrylate) and 8 parts of an impact strength modifier (terpolymer of methylmethacrylate, styrene and butadiene) is rolled on a mixer roll for 5 minutes at 180° C. Samples having a thickness of 0.3 mm are taken from the rolled sheet obtained. The samples are subjected to heat in an oven at 180° C. and every 10 minutes the thermal ageing of a sample is determined according to the Yellowness Index (YI) of ASTM D 1925-70. The results are reported in the following table.

| Yellowness Index after | | | | | | | | |
|---|---|---|---|---|---|---|---|---|
| 0 min. | 10 min. | 20 min. | 30 min. | 40 min. | 50 min. | 60 min. | 70 min. | 80 min. |
| 6,2 | 25 | 38 | 42 | 50 | 77 | 89 | >100 | |

What is claimed is:
1. A chlorine-containing thermoplastic, containing a pyrrole of the formula I

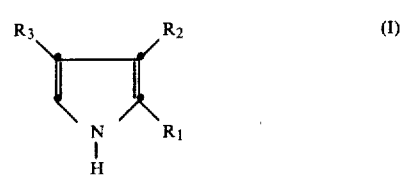

in which $R_1$ is hydrogen, alkyl, cycloalkyl, aryl, alkoxycarbonylmethyl, free or esterified α-hydroxyalkyl, free or esterified α-hydroxycycloalkylmethyl, free or esterified α-hydroxyaralkyl, alkoxymethyl, alkylthiomethyl, aryloxymethyl, arylthiomethyl, cycloalkoxymethyl, cycloalkylthiomethyl, aralkoxymethyl, aralkylthiomethyl, alkoxy, alkylthio, cycloalkoxy, cycloalkylthio, aralkoxy, arylalkylthio, aryloxy, arylthio, halogen, mercapto, mercaptomethyl or hydroxyl, $R_2$ is hydrogen, alkyl, cycloalkyl, aryl, free or esterified α-hydroxyalkyl, in which the alkyl moiety together with $R_1$ can be alkylene, or free or esterified α-hydroxycycloalkylmethyl, free or esterified α-hydroxyaralkyl, alkoxy, cycloalkoxy, aralkoxy, aryloxy, alkylthio, cycloalkylthio, aralkylthio, arylthio, alkoxymethyl, alkylthiomethyl, aryloxymethyl, arylthiomethyl, cycloalkoxymethyl, cycloalkylthiomethyl, aralkoxymethyl, aralkylthiomethyl, hydroxyl, cyano, free carboxyl or carboxyl in the form of a salt or an ester, or acyl, it being possible for acyl together with $R_1$ to be —CO-alkylene, in which —CO— is bonded in the 3-position, or $R_2$ is halogen, mercapto or mercaptomethyl, and $R_3$ is alkyl, cycloalkyl, aralkyl, aryl, free or esterified hydroxymethyl, alkoxymethyl, alkylthiomethyl, cycloalkoxymethyl, cycloalkylthiomethyl, aralkoxymethyl, aralkylthiomethyl, aryloxymethyl or arylthiomethyl, alkoxy, alkylthio, cycloalkoxy, cycloalkylthio, aralkoxy, aralkylthio, aryloxy, arylthio, halogen, mercapto or mercaptomethyl, or if $R_2$ is carboxyl in the form of a salt, $R_3$ is hydrogen and $R_1$ is as defined, or in which $R_3$ is hydroxyl and $R_1$ is hydrogen, alkyl or aryl and $R_2$ is hydrogen, alkyl, aryl or acyl, or a salt thereof, and at least one costabilizer selected of the group consisting of epoxy compounds, phosphites, metal carboxylate or phenolate stabilizers and organo-tin compounds; the weight ratio of pyrrole to costabilizer being from about 2:1 to 1:8.

2. A chlorine-containing thermoplastic according to claim 1, containing a pyrrole of the formula I and at least one epoxy compound or a metal carboxylate or phenolate of a metal of the second main group of the Periodic Table.

3. A chlorine-containing thermoplastic according to claim 1, containing a pyrrole of the formula I and at least one phosphite.

4. A chlorine-containing thermoplastic according to claim 2 containing additionally at least one phosphite.

5. A chlorine-containing thermoplastic according to claim 2 containing additionally at least one zinc or cadmium carboxylate or an organo-tin compound.

6. A chlorine-containing thermoplastic according to claim 5, containing additionally at least one phosphite.

* * * * *